(12) United States Patent
Lion et al.

(10) Patent No.: US 7,794,695 B2
(45) Date of Patent: Sep. 14, 2010

(54) NON-TRANSFER COSMETIC COMPOSITION COMPRISING A DISPERSION OF PARTICLES OF A SILICON-FREE GRAFTED ETHYLENE POLYMER IN A LIQUID FATTY PHASE

(75) Inventors: Bertrand Lion, Paris (FR); Xavier Blin, Paris (FR); Nathalie Jager Lezer, Verrières-le-Buisson (FR)

(73) Assignee: L'Oreal S.A., Paris (FR)

( * ) Notice: Subject to any disclaimer, the term of this patent is extended or adjusted under 35 U.S.C. 154(b) by 1285 days.

(21) Appl. No.: 10/538,783

(22) PCT Filed: Dec. 12, 2003

(86) PCT No.: PCT/FR03/03714

§ 371 (c)(1),
(2), (4) Date: Jan. 9, 2006

(87) PCT Pub. No.: WO2004/055082

PCT Pub. Date: Jul. 1, 2004

(65) Prior Publication Data

US 2006/0127341 A1 Jun. 15, 2006

(30) Foreign Application Priority Data

Dec. 12, 2002 (FR) .................. 02 15737
Dec. 12, 2002 (FR) .................. 02 15738
Dec. 12, 2002 (FR) .................. 02 15739

(51) Int. Cl.
*A61Q 1/06* (2006.01)
*A61Q 1/04* (2006.01)
*A61Q 1/10* (2006.01)

(52) U.S. Cl. .................. 424/64; 424/70.7; 424/401

(58) Field of Classification Search .................. None
See application file for complete search history.

(56) References Cited

U.S. PATENT DOCUMENTS

| | | | |
|---|---|---|---|
| 4,887,622 A | 12/1989 | Gueret | |
| 5,492,426 A | 2/1996 | Gueret | |
| 5,625,005 A | 4/1997 | Mallya et al. | |
| 5,772,347 A | 6/1998 | Gueret | |
| 5,851,517 A | 12/1998 | Mougin et al. | |
| 5,879,095 A | 3/1999 | Gueret | |
| 6,059,473 A | 5/2000 | Gueret | |
| 6,139,826 A | 10/2000 | Schraer et al. | |
| 6,254,877 B1* | 7/2001 | De La Poterie et al. | 424/401 |
| 6,328,495 B1 | 12/2001 | Gueret | |
| 6,403,106 B1* | 6/2002 | Sebag et al. | 424/401 |
| 6,412,496 B1 | 7/2002 | Gueret | |
| 6,484,731 B1 | 11/2002 | Lacout | |
| 6,506,376 B2* | 1/2003 | Sato | 424/78.03 |
| 6,534,047 B1 | 3/2003 | Bodelin | |
| 6,692,173 B2 | 2/2004 | Gueret | |
| 6,843,611 B2 | 1/2005 | Blondeel et al. | |
| 7,378,013 B2* | 5/2008 | Sandler | 280/507 |
| 2002/0015611 A1 | 2/2002 | Blondeel et al. | |
| 2002/0054783 A1 | 5/2002 | Gueret | |
| 2005/0002724 A1 | 1/2005 | Blondeel et al. | |
| 2005/0276779 A1* | 12/2005 | Blin | 424/70.16 |
| 2005/0281769 A1* | 12/2005 | Toumi | 424/70.11 |
| 2006/0134034 A1* | 6/2006 | Blin et al. | 424/64 |
| 2007/0224158 A1* | 9/2007 | Cassin et al. | 424/78.03 |

FOREIGN PATENT DOCUMENTS

| | | |
|---|---|---|
| EP | 096 459 | 12/1983 |
| EP | 749 747 | 12/1996 |
| EP | 895 467 | 12/1999 |
| EP | 1 064 919 | 1/2001 |
| FR | 2 722 380 | 1/1996 |
| FR | 2 727 609 | 6/1996 |
| FR | 2 746 640 | 10/1997 |
| FR | 2 761 959 | 10/1998 |
| FR | 2 775 566 | 9/1999 |
| FR | 2 791 042 | 9/2000 |
| FR | 2 792 190 | 10/2000 |
| FR | 2 792 618 | 10/2000 |
| FR | 2 796 529 | 1/2001 |
| FR | 2 806 273 | 9/2001 |
| WO | WO 97/17057 | 5/1997 |
| WO | WO97/33556 | * 9/1997 |
| WO | WO 97/35541 | * 10/1997 |
| WO | WO 00/28948 | 5/2000 |
| WO | WO 01/03538 | 1/2001 |
| WO | WO 03/018423 | 3/2003 |

OTHER PUBLICATIONS

English Language Derwent Abstract for FR 2 775 566.
English Language Derwent Abstract for FR 2 792 190.
English Language Derwent Abstract for WO 01/03538.
Grulke, "Solubility parameter values," *Polymer Handbook*, 3$^{rd}$ edition, Chapter VII, pp. 519-559, Oct. 1989.
Hansen, "The three-dimensional solubility parameters," *J. Paint. Technol.*, 39:105 (1967).
Gillman, *Polymer Letters*, vol. 5, pp. 477-481 (1967).
Prince, "Microemulsions Theory and Practice," *Academic Press*, pp. 21-32 (1977).
Kirk-Othmer, *Encyclopedia of Chemical Technology*, 3$^{rd}$ edition, vol. 22, pp. 347-377 (Wiley 1979).
Hulst, "Light Scattering by Small Particles," Chapters 9-10, (Wiley 1957).
International Search Report for PCT/FR 03/03714 (the present application).

* cited by examiner

*Primary Examiner*—Jyothsna A Venkat
(74) *Attorney, Agent, or Firm*—Finnegan, Henderson, Farabow, Garrett & Dunner LLP

(57) ABSTRACT

The invention relates to a cosmetic composition comprising, in a cosmetically acceptable medium, at least one dispersion of particles of a non-silicone-based grafted ethylenic polymer in a liquid fatty phase.

Use for making up and caring for keratin materials, especially the skin and the lips.

8 Claims, No Drawings

NON-TRANSFER COSMETIC COMPOSITION COMPRISING A DISPERSION OF PARTICLES OF A SILICON-FREE GRAFTED ETHYLENE POLYMER IN A LIQUID FATTY PHASE

The present invention relates to a cosmetic composition comprising a dispersion of particles of a non-silicone-based grafted ethylenic polymer in a liquid fatty phase, which is intended to be applied to human keratin materials, for instance the skin, the lips or the nails, or keratin fibres such as the eyelashes, the eyebrows or the hair.

The composition according to the invention may be a makeup composition or a care composition for keratin materials, in particular for the skin, the lips and keratin fibres, especially the eyelashes, and preferably a makeup composition.

The makeup composition may be a lip makeup product (lipstick), a foundation, an eyeshadow, a makeup rouge, a concealer product, an eyeliner, a body makeup product, a mascara, a nail varnish or a hair makeup product.

The care composition may be a body and facial skin care product, especially an antisun product or a skin-colouring product (such as a self-tanning product). The composition may also be a haircare product, especially for holding the hairstyle or shaping the hair, or alternatively an eyelash care product.

Lipstick and foundation compositions are commonly used to give the lips or the skin, and especially the face, an aesthetic colour. These makeup products generally contain fatty phases such as waxes and oils, pigments and/or fillers and optionally additives, for instance cosmetic or dermatological active agents.

When they are applied to the skin, these compositions have the drawback of transferring, i.e. of becoming at least partially deposited, and leaving marks, on certain supports with which they may come into contact and especially a glass, a cup, a cigarette, an item of clothing or the skin. This results in mediocre persistence of the applied film, making it necessary to regularly renew the application of the foundation or lipstick composition. Moreover, the appearance of these unacceptable marks, especially on blouse collars, may put certain women off using this type of makeup.

"Transfer-resistant" lip and skin makeup compositions are thus sought, which have the advantage of forming a deposit that does not become at least partially deposited onto the supports with which they come into contact (glass, clothing, cigarette or fabric).

To limit the transfer of cosmetic compositions, it is known practice to use volatile oils, especially in contents of greater than 40% by weight. These volatile oils present in large amount render the makeup product, especially lipstick, uncomfortable for the user: the makeup deposit gives a sensation of drying-out and of tautness.

Products in the form of two separate compositions to be applied one over the other onto the lips to obtain transfer-resistant makeup are also known. For example, the product Lip Finity from Max Factor is a two-coat product, the base composition (known as the base coat) of which contains a silicone resin and volatile oils, and the surface composition (known as the top coat) of which contains a sucrose ester (as described in patent application WO 97/17057) to improve the comfort of the transfer-resistant makeup product. However, the need to apply two compositions to make up the face may be unacceptable for certain users.

The aim of the present invention is to provide a novel route for the formulation of a cosmetic composition, especially a makeup composition, which makes it possible to obtain a deposit that has good transfer-resistance properties, especially without using a large content of volatile oils, and without requiring the application of two different compositions to obtain the result.

The aim of the invention is also to provide a cosmetic composition, especially a makeup composition, which makes it possible to obtain a comfortable deposit on the skin, the lips or keratin fibres.

The inventors have discovered that it is possible to obtain such a composition by using a dispersion of particles of a non-silicone-based grafted ethylenic polymer in a liquid fatty phase as described hereinbelow. The composition makes it possible to obtain a deposit, especially makeup on keratin materials, in particular on the skin, the lips or keratin fibres, which has good transfer-resistance properties. Furthermore, the deposit obtained on the skin or the lips does not cause the user any sensation of drying-out or of tautness: the deposit is thus comfortable.

One subject of the present invention is thus, more specifically, a cosmetic composition comprising, in a cosmetically acceptable medium, at least one dispersion of particles, preferably solid particles, of a non-silicone-based grafted ethylenic polymer in a liquid fatty phase as described hereinbelow, the composition especially being as defined hereinbelow.

Advantageously, according to a first embodiment of the composition according to the invention, the polymer is such that, when it is dispersed in sufficient amount in the composition, the said composition is capable of forming a deposit that has a transfer index of less than or equal to 35%.

Advantageously, the composition according to the invention is capable of forming a deposit that has a transfer index of less than or equal to 30%, preferably less than or equal to 25%, preferably less than or equal to 20%, preferably less than or equal to 15%, preferably less than or equal to 10% and preferably less than or equal to 5%.

A subject of the invention is also a non-therapeutic cosmetic process for making up or caring for keratin materials, in particular the skin, the lips or keratin fibres, comprising the application to the keratin materials, in particular to the skin or the lips, of a composition as defined above.

A subject of the invention is also the use of a composition as defined above, to obtain a transfer-resistant deposit, especially transfer-resistant makeup, on keratin materials, in particular on the skin, the lips or keratin fibres.

A subject of the invention is also the use of a dispersion of particles of a non-silicone-based grafted ethylenic polymer in a liquid fatty phase as defined above, in a cosmetic composition comprising a cosmetically acceptable organic liquid medium, to obtain a transfer-resistant deposit, especially transfer-resistant makeup, on keratin materials, in particular on the skin, the lips or keratin fibres.

The transfer of the deposit obtained with the composition according to the invention is determined according to the protocol described hereinbelow.

A support (rectangle of 40 mm×70 mm and 3 mm thick) of polyethylene foam that is adhesive on one of the faces, having a density of 33 kg/m$^3$ (sold under the name RE40X70EP3 from the company Joint Technique Lyonnais Ind) is preheated on a hotplate maintained at a temperature of 40° C. in order for the surface of the support to be maintained at a temperature of 33° C.±1° C.

The composition is applied over the entire non-adhesive surface of the support, by spreading it using a fine brush to obtain a deposit of about 15 μm of the composition, while leaving the support on the hotplate, and the support is then left to dry for 30 minutes.

After drying, the support is bonded via its adhesive face onto an anvil of diameter 20 mm and equipped with a screw pitch. The support/deposit assembly is then cut up using a punch 18 mm in diameter. The anvil is then screwed onto a press (Statif Manuel Imada SV-2 from the company Someco) equipped with a tensile testing machine (Imada DPS-20 from the company Someco).

White photocopier paper of 80 g/m$^2$ is placed on the bed of the press and the support/deposit assembly is then pressed on the paper at a pressure of 2.5 kg for 30 seconds. After removing the support/deposit assembly, some of the deposit is transferred onto the paper. The colour of the deposit transferred onto the paper is then measured using a Minolta CR300 calorimeter, the colour being characterized by the L*, a*, b* colorimetric parameters. The colorimetric parameters $L^*_0$, $a^*_0$ and $b^*_0$ of the colour of the plain paper used is determined.

The difference in colour ΔE1 between the colour of the deposit transferred relative to the colour of the plain paper is then determined by means of the following relationship.

$$\Delta E1 = \sqrt{(L^* - L_0^*)^2 + (a^* - a_0^*)^2 + (b^* - b_0^*)^2}$$

Moreover, a total transfer reference is prepared by applying the composition directly onto a paper identical to the one used previously, at room temperature (25° C.), by spreading the composition using a fine brush and so as to obtain a deposit of about 15 μm of the composition, and the deposit is then left to dry for 30 minutes at room temperature (25° C.). After drying, the colorimetric parameters $L^{*\prime}$, $a^{*\prime}$ and $b^{*\prime}$ of the colour of the deposit placed on the paper, corresponding to the reference colour of total transfer, is measured directly. The colorimetric parameters $L^{*\prime}_0$, $a^{*\prime}_0$ and $b^{*\prime}_0$ of the colour of the plain paper used are determined.

The difference in colour ΔE2 between the reference colour of total transfer relative to the colour of the plain paper is then determined by means of the following relationship.

$$\Delta E2 = \sqrt{(L^{*\prime} - L_0^{*\prime})^2 + (a^{*\prime} - a_0^{*\prime})^2 + (b^{*\prime} - b_0^{*\prime})^2}$$

The transfer of the composition, expressed as a percentage, is equal to the ratio:

100×ΔE1/ΔE2

The measurement is performed on 4 supports in succession and the transfer value corresponds to the mean of the 4 measurements obtained with the 4 supports.

The composition according to the invention comprises a dispersion of particles of non-silicone-based grafted ethylenic polymer.

The term "ethylenic polymer" means a polymer obtained by polymerization of ethylenically unsaturated monomers.

The term "non-silicone-based grafted polymer" means a grafted polymer predominantly containing a carbon-based macromonomer and optionally containing up to 7% by weight and preferably up to 5% by weight of silicone-based macromonomer, or even being free of silicone-based macromonomer. The dispersion of non-silicone-based grafted ethylenic polymer is especially free of stabilizing polymer different from the said grafted polymer, such as those described in EP 749 747, and the particles of grafted ethylenic polymer are therefore not surface-stabilized with such additional stabilizing polymers. The grafted polymer is therefore dispersed in the liquid fatty phase in the absence of additional surface stabilizer for the particles.

The term "grafted polymer" means a polymer having a skeleton comprising at least one side chain that is pendent or located at the end of a chain, and preferably pendent.

Advantageously, the non-silicone-based grafted ethylenic polymer comprises an ethylenic skeleton that is insoluble in the said liquid fatty phase, and side chains covalently bonded to the said skeleton, which are soluble in the liquid fatty phase.

The non-silicone-based grafted ethylenic polymer is especially a non-crosslinked polymer. In particular, the polymer is obtained by polymerization of monomers comprising only one polymerizable group.

The non-silicone-based grafted ethylenic polymer is preferably a film-forming polymer. The term "film-forming polymer" means a polymer capable, by itself or in the presence of an auxiliary film-forming agent, of forming a continuous film, especially to the eye or to the touch, which adheres to a support, especially to keratin materials.

According to one embodiment of the invention, the grafted ethylenic polymer is a grafted acrylic polymer.

The non-silicone-based grafted ethylenic polymer may especially be obtained by free-radical polymerization in an organic polymerization medium:
- of at least one ethylenic monomer, in particular of at least one acrylic monomer and optionally of at least one additional non-acrylic vinyl monomer, to form the said insoluble skeleton; and
- of at least one macromonomer comprising a polymerizable end group to form the side chains, the said macromonomer having a weight-average molecular mass of greater than or equal to 200 and the content of polymerized macromonomer representing from 0.05% to 20% by weight of the polymer.

The liquid fatty phase may contain the organic polymerization medium.

The organic liquid dispersion medium, corresponding to the medium in which the grafted polymer is supplied, may be identical to the polymerization medium.

However, the polymerization medium may be totally or partially replaced with another organic liquid medium. This other organic liquid medium may be added, after polymerization, to the polymerization medium. The said polymerization medium is then totally or partially evaporated.

The liquid fatty phase may contain liquid organic compounds other than those present in the dispersion medium. These other compounds are chosen such that the grafted polymer remains in dispersed form in the liquid fatty phase.

The organic liquid dispersion medium is present in the liquid fatty phase of the composition according to the invention due to the introduction into the composition of the dispersion of grafted polymer obtained.

Liquid Fatty Phase:

The liquid fatty phase comprises, preferably predominantly, one or more liquid organic compounds (or oils) as defined below.

In particular, the liquid fatty phase is a non-aqueous liquid organic phase that is immiscible with water at room temperature (25° C.).

The term "liquid organic compound" means a non-aqueous compound that is in liquid form at room temperature (25° C.) and therefore flows under its own weight.

The term "silicone compound" means a compound containing at least one silicon atom.

The composition according to the invention advantageously contains a volatile oil as described below.

The term "volatile oil" means an oil capable of evaporating from the skin or the lips in less than one hour, especially having a vapour pressure, at room temperature and atmospheric pressure, ranging from $10^{-3}$ to 300 mmHg (0.13 Pa to 40 000 Pa).

The volatile oil may be silicone-based or non-silicone-based. It may be chosen especially from octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane, decamethyltetrasiloxane, isododecane, isodecane and isohexadecane, and mixtures thereof.

The volatile oil is advantageously present in a content ranging from 1% to 70% by weight, preferably ranging from 5% to 50% by weight and preferentially ranging from 10% to 35% by weight, relative to the total weight of the composition.

The liquid fatty phase may contain a non-volatile oil as described below. The non-volatile oil is advantageously present in a content ranging from 1% to 80% by weight, preferably ranging from 5% to 60% by weight and preferentially ranging from 10% to 50% by weight, relative to the total weight of the composition.

Among the liquid organic compounds or oils that may be present in the liquid organic dispersion medium, mention may be made of:

liquid organic compounds, especially silicone-based or non-silicone-based, having a global solubility parameter according to the Hansen solubility space of less than or equal to 18 $(MPa)^{1/2}$ and preferably less than or equal to 17 $(MPa)^{1/2}$, monoalcohols having a global solubility parameter according to the Hansen solubility space of less than or equal to 20 $(MPa)^{1/2}$, and mixtures thereof.

The global solubility parameter $\delta$ according to the Hansen solubility space is defined in the article "Solubility parameter values" by Eric A. Grulke in the book "Polymer Handbook", 3rd Edition, Chapter VII, p. 519-559, by the relationship:

$$\delta = (d_D^2 + d_P^2 + d_H^2)^{1/2}$$

in which $d_D$ characterizes the London dispersion forces arising from the formation of dipoles induced during molecular impacts, $d_P$ characterizes the Debye interaction forces between permanent dipoles, and $d_H$ characterizes the forces of specific interactions (such as hydrogen bonding, acid/base, donor/acceptor, etc.).

The definition of solvents in the solubility space according to Hansen is described in the article by C. M. Hansen: "The three-dimensional solubility parameters", J. Paint Technol. 39, 105 (1967).

Among the liquid organic compounds, especially silicone-based or non-silicone-based, having a global solubility parameter according to the Hansen solubility space of less than or equal to 18 $(MPa)^{1/2}$, mention may be made of liquid fatty substances, especially oils, which may be chosen from natural or synthetic, carbon-based, hydrocarbon-based, fluoro and silicone oils, which are optionally branched, alone or as a mixture.

Among these oils, mention may be made of plant oils formed from fatty acid esters and from polyols, in particular triglycerides, such as sunflower oil, sesame oil or rapeseed oil, or esters derived from acids or alcohols containing a long chain (i.e. a chain containing from 6 to 20 carbon atoms), in particular the esters of formula RCOOR' in which R represents a higher fatty acid residue containing from 7 to 19 carbon atoms and R' represents a hydrocarbon-based chain containing from 3 to 20 carbon atoms, such as palmitates, adipates and benzoates, in particular diisopropyl adipate.

Mention may also be made of linear, branched and/or cyclic alkanes, which may be volatile, and in particular liquid paraffin, liquid petroleum jelly or hydrogenated polyisobutylene, isododecane or "Isopars", volatile isoparaffins. Mention may also be made of esters, ethers and ketones.

Mention may also be made of silicone oils such as polydimethylsiloxanes and polymethylphenyl-siloxanes, optionally substituted with aliphatic and/or aromatic groups, which are optionally fluorinated, or with functional groups such as hydroxyl, thiol and/or amine groups, and volatile silicone oils, which are especially cyclic.

In particular, mention may be made of volatile and/or non-volatile, optionally branched silicone oils.

The term "volatile oil" means an oil capable of evaporating from the skin or the lips in less than one hour, and especially having a vapour pressure, at room temperature and atmospheric pressure, ranging from $10^{-3}$ to 300 mmHg (0.13 Pa to 40 000 Pa).

As volatile silicone oils that may be used in the invention, mention may be made of linear or cyclic silicones containing from 2 to 7 silicon atoms, these silicones optionally comprising alkyl or alkoxy groups containing from 1 to 10 carbon atoms. Mention may be made in particular of octamethylcyclotetrasiloxane, decamethylcyclopentasiloxane, dodecamethylcyclohexasiloxane, heptamethylhexyltrisiloxane, heptamethyl-octyltrisiloxane, octamethyltrisiloxane and decamethyltetrasiloxane, and mixtures thereof.

Among the non-volatile silicone oils that may be mentioned are non-volatile polydialkylsiloxanes, such as non-volatile polydimethylsiloxanes (PDMS); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyl trimethylsiloxy diphenylsiloxanes, diphenyl dimethicones, diphenyl methyldiphenyltrisiloxanes and polymethyl-phenylsiloxanes; polysiloxanes modified with fatty acids (especially of $C_8$-$C_{20}$), fatty alcohols (especially of $C_8$-$C_{20}$) or polyoxyalkylenes (especially polyoxy-ethylene and/or polyoxypropylene); amino polysiloxanes; polysiloxanes containing hydroxyl groups; fluoro poly-siloxanes comprising a fluorinated group that is pendent or at the end of a silicone chain, containing from 1 to 12 carbon atoms, all or some of the hydrogen atoms of which are replaced with fluorine atoms; and mixtures thereof.

As non-silicone-based liquid organic compounds with a global solubility parameter according to the Hansen solubility space of less than or equal to 18 $(MPa)^{1/2}$, mention may be made in particular of:

linear, branched or cyclic esters containing at least 6 carbon atoms, especially 6 to 30 carbon atoms;

ethers containing at least 6 carbon atoms, especially 6 to 30 carbon atoms; and ketones containing at least 6 carbon atoms, especially 6 to 30 carbon atoms.

The expression "liquid monoalcohols having a global solubility parameter according to the Hansen solubility space of less than or equal to 20 $(MPa)^{1/2}$", means aliphatic fatty liquid monoalcohols containing 6 to 30 carbon atoms, the hydrocarbon-based chain not comprising a substitution group. Monoalcohols according to the invention that may be mentioned include oleyl alcohol, decanol, octyldodecanol and linoleyl alcohol.

Non-silicone-based Medium

According to a first embodiment of the invention, the liquid fatty phase may be a non-silicone-based liquid fatty phase.

The term "non-silicone-based liquid fatty phase" means a fatty phase comprising one or more non-silicone-based liquid organic compounds or oils, such as those mentioned above, the said non-silicone-based compounds being predominantly present in the liquid fatty phase, i.e. to at least 50% by weight, especially from 50% to 100% by weight, preferably from 60% to 100% by weight (for example from 60% to 99% by weight), or alternatively from 65% to 100% by weight (for example from 65% to 95% by weight), relative to the total weight of the liquid fatty phase.

The non-silicone-based liquid organic compounds may especially be chosen from:

non-silicone-based liquid organic compounds with a global solubility parameter according to the Hansen solubility space of less than or equal to 18 $(MPa)^{1/2}$;

monoalcohols with a global solubility parameter according to the Hansen solubility space of less than or equal to 20 $(MPa)^{1/2}$; and mixtures thereof.

The said non-silicone-based liquid fatty phase may thus optionally comprise silicone-based liquid organic compounds or oils, such as those mentioned previously, which may be present in an amount of less than 50% by weight, especially ranging from 0.1% to 40% by weight, or even ranging from 1% to 35% by weight, or alternatively ranging from 5% to 30% by weight, relative to the total weight of the liquid fatty phase.

According to one particular embodiment of the invention, the non-silicone-based liquid fatty phase does not contain any silicone-based liquid organic compounds or oils.

When the liquid fatty phase is a non-silicone-based liquid fatty phase, the macromonomers present in the grafted polymer are advantageously carbon-based macromonomers as described below.

Silicone-based Medium:

According to a second embodiment of the invention, the liquid fatty phase may be a silicone-based liquid fatty phase.

The term "silicone-based liquid fatty phase" means a fatty phase comprising one or more silicone-based liquid organic compounds or silicone oils such as those described previously, the said silicone compounds being predominantly present in the liquid fatty phase, i.e. to at least 50% by weight, especially from 50% to 100% by weight, preferably from 60% to 100% by weight (for example from 60% to 99% by weight), or else from 65% to 100% by weight (for example from 65% to 95% by weight), relative to the total weight of the liquid fatty phase.

The silicone-based liquid organic compounds may especially be chosen from:

liquid organic compounds, which are especially non-silicone-based or silicone-based, with a global solubility parameter according to the Hansen solubility space of less than or equal to 18 $(MPa)^{1/2}$.

The said silicone-based liquid fatty phase may thus optionally comprise non-silicone-based liquid organic compounds or oils, as described previously, which may be present in an amount of less than 50% by weight, especially ranging from 0.1% to 40% by weight, or even ranging from 1% to 35% by weight, or else ranging from 5% to 30% by weight, relative to the total weight of the liquid fatty phase.

According to one particular embodiment of the invention, the silicone-based liquid fatty phase does not contain any non-silicone-based liquid organic compounds.

Grafted Polymer:

The choice of monomers constituting the skeleton of the polymer, of macromonomers, the molecular weight of the polymer, and the proportion of the monomers and macromonomers may be made as a function of the liquid organic dispersion medium so as advantageously to obtain a dispersion of particles of grafted polymers, in particular a stable dispersion, this choice possibly being made by a person skilled in the art.

The term "stable dispersion" means a dispersion that is not liable to form a solid deposit or to undergo liquid/solid phase separation, especially after centrifugation, for example at 4000 rpm for 15 minutes.

The non-silicone-based grafted ethylenic polymer forming the particles in dispersion thus comprises a skeleton that is insoluble in the said dispersion medium and a portion that is soluble in the said dispersion medium.

The grafted ethylenic polymer may be a random polymer.

According to the invention, the term "grafted ethylenic polymer" means a polymer that may be obtained by free-radical polymerization:

of one or more ethylenic monomer(s);

with one or more macromonomer(s), in an organic polymerization medium.

According to the invention, the term "grafted acrylic polymer" means a polymer that may be obtained by free-radical polymerization:

of one or more acrylic monomer(s), and optionally of one or more additional non-acrylic vinyl monomer(s);

with one or more macromonomer(s), in an organic polymerization medium.

Advantageously, the acrylic monomers represent from 50% to 100% by weight, preferably from 55% to 100% by weight (especially from 55% to 95% by weight) and preferentially from 60% to 100% by weight (especially from 60% to 90% by weight) of the mixture of acrylic monomers+optional non-acrylic vinyl monomers.

Preferably, the acrylic monomers are chosen from monomers whose homopolymer is insoluble in the dispersion medium under consideration, i.e. the homopolymer is in solid (or non-dissolved) form at a concentration of greater than or equal to 5% by weight at room temperature (20° C.) in the said dispersion medium.

Macromonomers:

According to the invention, the expression "macromonomer containing a polymerizable end group" means any polymer comprising on only one of its ends a polymerizable end group capable of reacting during the polymerization reaction with acrylic monomers and optionally the additional non-acrylic vinyl monomers constituting the skeleton. The macromonomer makes it possible to form the side chains of the grafted acrylic polymer. The polymerizable group of the macromonomer may advantageously be an ethylenically unsaturated group capable of free-radical polymerization with the monomers constituting the skeleton.

The macromonomer is a carbon-based macromonomer.

The term "carbon-based macromonomer" means a non-silicone-based macromonomer and especially an oligomeric macromonomer obtained by polymerization of ethylenically unsaturated non-silicone-based monomer(s), and mainly by polymerization of acrylic and/or non-acrylic vinyl monomers.

The term "silicone-based macromonomer" means an organopolysiloxane macromonomer and in particular a polydimethylsiloxane macromonomer.

Preferably, the macromonomer is chosen from macromonomers whose homopolymer is soluble in the dispersion medium under consideration, i.e. fully dissolved at a concentration of greater than or equal to 5% by weight and at room temperature in the said dispersion medium.

Thus, the grafted acrylic polymer comprises a skeleton (or main chain) consisting of a sequence of acrylic units resulting from the polymerization especially of one or more acrylic monomers and of side chains (or grafts) derived from the reaction of the macromonomers, the said side chains being covalently bonded to the said main chain.

The skeleton (or main chain) is insoluble in the dispersion medium under consideration, whereas the side chains (or grafts) are soluble in the said dispersion medium.

Monomers:

In the present patent application, the term "acrylic monomers" means monomers chosen from (meth)-acrylic acid, (meth)acrylic acid esters (also known as (meth)acrylates), and (meth)acrylic acid amides (also known as (meth)acrylamides).

As acrylic monomers that may be used to constitute the insoluble skeleton of the polymer, mention may be made, alone or as a mixture, of the following monomers, and also the salts thereof:

(i) the (meth)acrylates of formula:

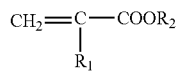

in which:
$R_1$ denotes a hydrogen atom or a methyl group;
$R_2$ represents a group chosen from:
- a linear or branched alkyl group containing from 1 to 6 carbon atoms, the said group possibly comprising in its chain one or more hetero atoms chosen from O, N and S; and/or possibly comprising one or more substituents chosen from —OH, halogen atoms (F, Cl, Br or I) and —NR'R" with R' and R", which may be identical or different, chosen from linear or branched $C_1$-$C_4$ alkyls; and/or possibly being substituted with at least one polyoxyalkylene group, in particular with $C_2$-$C_4$ alkylene, especially polyoxyethylene and/or polyoxypropylene, the said polyoxyalkylene group consisting of the repetition of 5 to 30 oxyalkylene units;
- a cyclic alkyl group containing from 3 to 6 carbon atoms, the said group possibly comprising in its chain one or more hetero atoms chosen from O, N and S, and/or possibly comprising one or more substituents chosen from OH and halogen atoms (F, Cl, Br or I).

Examples of $R_2$ that may be mentioned include the methyl, ethyl, propyl, butyl, isobutyl, methoxyethyl, ethoxyethyl, methoxypolyoxyethylene (350 OE), trifluoroethyl, 2-hydroxyethyl, 2-hydroxypropyl, dimethylaminoethyl, diethylaminoethyl or dimethylaminopropyl group;

(ii) the (meth)acrylamides of formula:

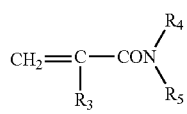

in which:
$R_3$ denotes a hydrogen atom or a methyl group;
$R_4$ and $R_5$, which may be identical or different, represent a hydrogen atom or a linear or branched alkyl group containing from 1 to 6 carbon atoms, which may comprise one or more substituents chosen from —OH, halogen atoms (F, Cl, Br or I) and —NR'R" with R' and R", which may be identical or different, chosen from linear or branched $C_1$-$C_4$ alkyls; or
$R_4$ represents a hydrogen atom and $R_5$ represents a 1,1-dimethyl-3-oxobutyl group.

As examples of alkyl groups that can constitute $R_4$ and $R_5$, mention may be made of n-butyl, t-butyl, n-propyl, dimethylaminoethyl, diethylaminoethyl and dimethylaminopropyl;

(iii) (meth)acrylic monomers comprising at least one carboxylic acid, phosphoric acid or sulfonic acid function, such as acrylic acid, methacrylic acid or acrylamidopropanesulfonic acid.

Among these acrylic monomers, those that may be mentioned most particularly are methyl, ethyl, propyl, butyl and isobutyl (meth)acrylates; methoxyethyl or ethoxyethyl (meth)acrylates; trifluoroethyl methacrylate; dimethylaminoethyl methacrylate, diethylaminoethyl methacrylate, 2-hydroxypropyl methacrylate, 2-hydroxyethyl methacrylate, 2-hydroxypropyl acrylate, 2-hydroxyethyl acrylate; dimethylaminopropylmethacrylamide; and the salts thereof; and mixtures thereof.

Preferably, the acrylic monomers are chosen from methyl acrylate, methoxyethyl acrylate, methyl methacrylate, 2-hydroxyethyl methacrylate, (meth)acrylic acid and dimethylaminoethyl methacrylate, and mixtures thereof.

Among the additional non-acrylic vinyl monomers that may be mentioned are:

vinyl esters of formula: $R_6$—COO—CH=$CH_2$ in which $R_6$ represents a linear or branched alkyl group containing from 1 to 6 atoms, or a cyclic alkyl group containing from 3 to 6 carbon atoms and/or an aromatic group, for example of benzene, anthracene or naphthalene type;

non-acrylic vinyl monomers comprising at least one carboxylic acid, phosphoric acid or sulfonic acid function, such as crotonic acid, maleic anhydride, itaconic acid, fumaric acid, maleic acid, styrenesulfonic acid, vinylbenzoic acid or vinylphosphoric acid, and the salts thereof;

non-acrylic vinyl monomers comprising at least one tertiary amine function, such as 2-vinylpyridine or 4-vinylpyridine;

and mixtures thereof.

Advantageously, the acrylic monomers present in the grafted polymer comprise at least (meth)acrylic acid and at least one monomer chosen from the (meth)acrylates and (meth)acrylamides described previously in points (i) and (ii). Preferably, the acrylic monomers comprise at least (meth)acrylic acid and at least one monomer chosen from $C_1$-$C_3$ alkyl (meth)acrylates. (Meth)acrylic acid may be present in a content of at least 5% by weight, especially ranging from 5% to 80% by weight, preferably of at least 10% by weight, especially ranging from 10% to 70% by weight, and preferentially of at least 15% by weight, especially ranging from 15% to 60% by weight, relative to the total weight of the polymer.

Among the salts that may be mentioned are those obtained by neutralization of acid groups with mineral bases such as sodium hydroxide, potassium hydroxide or ammonium hydroxide, or organic bases of alkanolamine type, for instance monoethanolamine, diethanolamine, triethanolamine or 2-methyl-2-amino-1-propanol.

Mention may also be made of the salts formed by neutralization of tertiary amine units, for example using a mineral or organic acid. Among the mineral acids that may be mentioned are sulfuric acid, hydrochloric acid, hydrobromic acid, hydriodic acid, phosphoric acid and boric acid. Among the organic acids that may be mentioned are acids comprising one or more carboxylic, sulfonic or phosphonic groups. They may be linear, branched or cyclic aliphatic acids, or alternatively aromatic acids. These acids may also comprise one or more hetero atoms chosen from O and N, for example in the form of hydroxyl groups. Acetic acid or propionic acid, terephthalic acid, and citric acid and tartaric acid may especially be mentioned.

According to one embodiment of the invention, the grafted ethylenic polymer contains no additional non-acrylic vinyl monomers as described above. In this embodiment, the insoluble skeleton of the grafted ethylenic polymer is formed solely from acrylic monomers as described previously.

It is understood that these non-polymerized acrylic monomers may be soluble in the dispersion medium under consideration, but the polymer formed with these monomers is insoluble in the dispersion medium.

Main acrylic monomers that may be used include methyl acrylate, methyl methacrylate, ethyl acrylate, ethyl methacrylate, n-propyl acrylate, n-propyl methacrylate, isopropyl acrylate and isopropyl methacrylate, and mixtures thereof.

Methyl acrylate, methyl methacrylate and ethyl methacrylate are most particularly preferred.

The additional acrylic monomers may be chosen from:
(meth)acrylic acid and its salts,
the (meth)acrylates of formula (I), and the salts thereof:

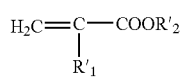

$$H_2C=C-COOR'_2 \quad (I)$$
$$\quad\quad |$$
$$\quad\quad R'_1$$

in which:
R'$_1$ denotes a hydrogen atom or a methyl group;
R'$_2$ represents
a linear or branched alkyl group containing from 1 to 6 carbon atoms, the said group comprising in its chain one or more oxygen atoms and/or comprising one or more substituents chosen from
OH, halogen atoms (F, Cl, Br or I) and —NR'R", with R' and R", which may be identical or different, being chosen from linear or branched C$_1$-C$_3$ alkyls;
a cyclic alkyl group containing from 3 to 6 carbon atoms, the said group possibly comprising in its chain one or more oxygen atoms and/or possibly comprising one or more substituents chosen from OH and halogen atoms (F, Cl, Br or I);
and mixtures thereof.

Examples of R'$_2$ that may be mentioned include the methoxyethyl, ethoxyethyl, trifluoroethyl, 2-hydroxyethyl, 2-hydroxypropyl, dimethylaminoethyl, diethylaminoethyl and dimethylaminopropyl groups.

Among these additional acrylic monomers, mention may be made most particularly of (meth)acrylic acid, methoxyethyl or ethoxyethyl (meth)acrylates; trifluoroethyl methacrylate; dimethylaminoethyl methacrylate, diethylaminoethyl methacrylate, 2-hydroxypropyl methacrylate, 2-hydroxyethyl methacrylate, 2-hydroxypropyl acrylate and 2-hydroxyethyl acrylate, the salts thereof, and mixtures thereof.

Acrylic acid and methacrylic acid are most particularly preferred.

The macromonomers comprise at one of the ends of the chain a polymerizable end group capable of reacting during the polymerization with the acrylic monomers and optionally the additional vinyl monomers, to form the side chains of the grafted ethylenic polymer. The said polymerizable end group may in particular be a vinyl or (meth)acrylate (or (meth) acryloxy) group, and preferably a (meth)acrylate group.

The macromonomers are preferably chosen from macromonomers whose homopolymer has a glass transition temperature (Tg) of less than or equal to 25° C., especially ranging from −100° C. to 25° C. and preferably ranging from −80° C. to 0° C.

The macromonomers have a weight-average molecular mass of greater than or equal to 200, preferably greater than or equal to 300, preferentially greater than or equal to 500 and more preferentially greater than 600.

Preferably, the macromonomers have a weight-average molecular mass (Mw) ranging from 200 to 100 000, preferably ranging from 500 to 50 000, preferentially ranging from 800 to 20 000, more preferentially ranging from 800 to 10 000 and even more preferentially ranging from 800 to 6000.

In the present patent application, the weight-average (Mw) and number-average (Mn) molar masses are determined by liquid gel permeation chromatography (THF solvent, calibration curve established with linear polystyrene standards, refractometric detector).

Carbon-based macromonomers that may in particular be mentioned include:
(i) homopolymers and copolymers of linear or branched C$_8$-C$_{22}$ alkyl (meth)acrylate, containing a polymerizable end group chosen from vinyl or (meth)acrylate groups, among which mention may be made in particular of: poly(2-ethylhexyl acrylate) macromonomers with a mono(meth)acrylate end group; poly(dodecyl acrylate) or poly(dodecyl methacrylate) macromonomers with a mono(meth)acrylate end group; poly(stearyl acrylate) or poly(stearyl methacrylate) macromonomers with a mono(meth)acrylate end group.

Such macromonomers are described in particular in patents EP 895 467 and EP 96459, and in the article by Gillman K. F., Polymer Letters, Vol 5, page 477-481 (1967).

Mention may be made in particular of macromonomers based on poly(2-ethylhexyl acrylate) or poly(dodecyl acrylate) with a mono(meth)acrylate end group;

(ii) polyolefins containing an ethylenically unsaturated end group, in particular containing a (meth)acrylate end group. Examples of such polyolefins that may be mentioned in particular include the following macromonomers, it being understood that they have a (meth)acrylate end group: polyethylene macromonomers, polypropylene macromonomers, macromonomers of polyethylene/polypropylene copolymer, macromonomers of polyethylene/polybutylene copolymer, polyisobutylene macromonomers; polybutadiene macromonomers; polyisoprene macromonomers; polybutadiene macromonomers; poly(ethylene/butylene)-polyisoprene macromonomers.

Such macromonomers are described in particular in U.S. Pat. No. 5,625,005, which mentions ethylene/butylene and ethylene/propylene macromonomers containing a (meth) acrylate reactive end group.

Mention may be made in particular of the poly(ethylene/ butylene) methacrylate such as that sold under the name Kraton Liquid L-1253 by Kraton Polymers.

Preferably, the polymerized macromonomer (constituting the side chains of the grafted polymer) represents from 0.1% to 15% by weight, preferably from 0.2% to 10% by weight and more preferably from 0.3% to 8% by weight, relative to the total weight of the polymer.

As particularly preferred grafted ethylenic polymer dispersed in a non-silicone-based liquid fatty phase, it is possible to use those obtained by polymerization:

- of methyl acrylate and of a polyethylene/polybutylene macromonomer containing a methacrylate end group (especially Kraton L-1253), in particular in a solvent chosen from isododecane, isononyl isononanoate, octyldodecanol, diisostearyl malate or a $C_{12}$-$C_{15}$ alkyl benzoate (such as Finsolv TN);
- of methoxyethyl acrylate and of a polyethylene/polybutylene macromonomer containing a methacrylate end group (especially Kraton L-1253), in particular in isododecane;
- of methyl acrylate/methyl methacrylate monomers and of a polyethylene/polybutylene macromonomer containing a methacrylate end group (especially Kraton L-1253), in particular in isododecane;
- of methyl acrylate/acrylic acidic monomers and of a polyethylene/polybutylene macromonomer containing a methacrylate end group (especially Kraton L-1253), in particular in isododecane;
- of methyl acrylate/dimethylaminoethyl methacrylate monomers and of a polyethylene/polybutylene macromonomer containing a methacrylate end group (especially Kraton L-1253), in particular in isododecane;
- of methyl acrylate/2-hydroxyethyl methacrylate monomers and of a polyethylene/polybutylene macromonomer containing a methacrylate end group (especially Kraton L-1253), in particular in isododecane.

The weight-average molecular mass (Mw) of the grafted polymer is preferably between 10 000 and 300 000, especially between 20 000 and 200 000 and better still between 25 000 and 150 000.

By virtue of the abovementioned characteristics, in a given organic dispersion medium, the polymers have the capacity to fold over on themselves, thus forming particles of substantially spherical shape, the periphery of these particles having the deployed side chains, which ensure the stability of these particles. Such particles resulting from the characteristics of the grafted polymer have the particular feature of not aggregating in the said medium and thus of being self-stabilized and of forming a particularly stable polymer particle dispersion.

In particular, the grafted ethylenic polymers of the dispersion are capable of forming nanometre-sized particles, with a mean size ranging from 10 to 400 nm and preferably from 20 to 200 nm.

As a result of this very small size, the grafted polymer particles in dispersion are particularly stable and therefore have little susceptibility to form aggregates.

The dispersion of grafted polymer may thus be a dispersion that is stable and does not form sediments when it is placed at room temperature (25° C.) for an extended period (for example 24 hours).

Preferably, the dispersion of grafted polymer particles has a solids content (or dry extract) of polymer of from 40% to 70% by weight of solids and especially from 45% to 65% by weight.

The dispersion of grafted polymer particles may be prepared via a process comprising a step of free-radical copolymerization, in an organic polymerization medium, of one or more acrylic monomers as defined above with one or more macromonomers as defined above.

As mentioned previously, the liquid organic dispersion medium may be identical to or different from the polymerization medium.

The copolymerization may be performed conventionally in the presence of a polymerization initiator. The polymerization initiators may be free-radical initiators. In general, such a polymerization initiator may be chosen from organic peroxide compounds such as dilauroyl peroxide, dibenzoyl peroxide or tert-butyl peroxy-2-ethylhexanoate; diazo compounds such as azobisisobutyronitrile or azobisdimethylvaleronitrile.

The reaction may also be initiated using photoinitiators or with radiation such as UV or neutrons, or with plasma.

In general, to perform this process, at least a portion of the organic polymerization medium, a portion of the additional acrylic and/or vinyl monomers, which will constitute the insoluble skeleton after polymerization, all of the macromonomer (which will constitute the side chains of the polymer) and a portion of the polymerization initiator are introduced into a reactor whose size is suitable for the amount of polymer to be prepared. At this stage of introduction, the reaction medium forms a relatively homogeneous medium.

The reaction medium is then stirred and heated up to a temperature to obtain polymerization of the monomers and macromonomers. After a certain time, the initially homogeneous and clear medium leads to a dispersion of milky appearance. A mixture consisting of the remaining portion of monomers and of the polymerization initiator is then added. After an adequate time during which the mixture is heated with stirring, the medium stabilizes in the form of a milky dispersion, the dispersion comprising polymer particles stabilized in the medium in which they have been created, the said stabilization being due to the presence, in the polymer, of side chains that are soluble in the said dispersion medium.

The grafted polymer may be present in the composition according to the invention in a solids content (or active material content) ranging from 1% to 70% by weight, better still from 5% to 60% by weight, preferably ranging from 6% to 45% and better still ranging from 8% to 40% by weight, relative to the total weight of the composition.

The composition according to the invention may also comprise at least one fatty substance that is solid at room temperature, especially chosen from waxes, pasty fatty substances and gums, and mixtures thereof. These fatty substances may be of animal, plant, mineral or synthetic origin.

Wax

The composition according to the invention may comprise a wax or a mixture of waxes.

The wax under consideration in the context of the present invention is generally a lipophilic compound that is solid at room temperature (25° C.), with a solid/liquid reversible change of state, having a melting point of greater than or equal to 30° C., which may be up to 120° C.

By bringing the wax to the liquid form (melting), it is possible to make it miscible with oils and to form a microscopically uniform mixture, but on bringing the mixture back to room temperature, recrystallization of the wax in the oils of the mixture is obtained.

In particular, the waxes that are suitable for the invention may have a melting point of greater than about 45° C. and in particular greater than 55° C.

The melting point of the wax may be measured using a differential scanning calorimeter (DSC), for example the calorimeter sold under the name DSC 30 by the company Mettler.

The measuring protocol is as follows:

A sample of 15 mg of product placed in a crucible is subjected to a first temperature rise ranging from 0° C. to 120° C., at a heating rate of 10° C./minute, it is then cooled from 120° C. to 0° C. at a cooling rate of 10° C./minute and is finally subjected to a second temperature increase ranging from 0° C. to 120° C. at a heating rate of 5° C./minute. During the second temperature increase, the variation of the difference in power absorbed by the empty crucible and by the crucible containing the sample of product is measured as a function of the temperature. The melting point of the compound is the temperature value corresponding to the top of the peak of the curve representing the variation in the difference in absorbed power as a function of the temperature.

The waxes that may be used in the compositions according to the invention are chosen from waxes that are solid and rigid at room temperature of animal, plant, mineral or synthetic origin, and mixtures thereof.

The wax may also have a hardness ranging from 0.05 MPa to 30 MPa, preferably ranging from 6 MPa to 15 MPa. The hardness is determined by measuring the compression force, measured at 20° C. using the texturometer sold under the name TA-XT2i by the company Rheo, equipped with a stainless-steel cylindrical spindle 2 mm in diameter, travelling at a measuring speed of 0.1 mm/s, and penetrating into the wax to a penetration depth of 0.3 mm.

The measuring protocol is as follows:

The wax is melted at a temperature equal to the melting point of the wax +20° C. The molten wax is poured into a container 30 mm in diameter and 20 mm deep. The wax is recrystallized at room temperature (25° C.) for 24 hours and is then stored for at least 1 hour at 20° C., before performing the hardness measurement. The hardness value is the maximum compression force measured, divided by the area of the texturometer spindle in contact with the wax.

Hydrocarbon-based waxes, for instance beeswax, lanolin wax, Chinese insect waxes, rice wax, carnauba wax, candelilla wax, ouricurry wax, esparto grass wax, cork fibre wax, sugar cane wax, Japan wax and sumach wax; montan wax, microcrystalline waxes, paraffins and ozokerite; polyethylene waxes, the waxes obtained by Fischer-Tropsch synthesis and waxy copolymers, and also esters thereof, may especially be used.

Mention may also be made of waxes obtained by catalytic hydrogenation of animal or plant oils containing linear or branched $C_8$-$C_{32}$ fatty chains.

Among these, mention may be made especially of hydrogenated jojoba oil, isomerized jojoba oil such as the partially hydrogenated trans isomerized jojoba oil manufactured or sold by the company Desert Whale under the commercial reference Iso-Jojoba-50®, hydrogenated sunflower oil, hydrogenated castor oil, hydrogenated coconut oil and hydrogenated lanolin oil, bis(1,1,1-trimethylolpropane) tetrastearate sold under the name "Hest 2T-4S" by the company Heterene and bis(1,1,1-trimethylolpropane) tetrabehenate sold under the name Hest 2T-4B by the company Heterene.

Mention may also be made of silicone waxes, for instance alkyl or alkoxy dimethicones containing from 16 to 45 carbon atoms, and fluoro waxes.

It is also possible to use the wax obtained by hydrogenation of olive oil esterified with stearyl alcohol, sold under the name "Phytowax Olive 18 L 57" or the waxes obtained by hydrogenation of castor oil esterified with cetyl alcohol, sold under the name "Phytowax Ricin 16L64 and 22L73" by the company Sophim. Such waxes are described in patent application FR-A-2 792 190.

According to one particular embodiment, the compositions according to the invention may comprise at least one "tacky" wax, i.e. a wax with a tack of greater than or equal to 0.7 N.s and a hardness of less than or equal to 3.5 MPa.

The use of a tacky wax may especially make it possible to obtain a cosmetic composition that is easy to apply to keratin fibres, shows good attachment to the keratin fibres and leads to the formation of a smooth, uniform and thickening makeup result.

The tacky wax used may especially have a tack ranging from 0.7 N.s to 30 N.s, in particular greater than or equal to 1 N.s, especially ranging from 1 N.s to 20 N.s, in particular greater than or equal to 2 N.s, especially ranging from 2 N.s to 10 N.s and in particular ranging from 2 N.s to 5 N.s.

The tack of the wax is determined by measuring the change in force (compression force or stretching force) as a function of time, at 20° C., using the texturometer sold under the name "TA-TX2i®" by the company Rheo, equipped with a conical acrylic polymer spindle forming an angle of 45°.

The measuring protocol is as follows:

The wax is melted at a temperature equal to the melting point of the wax +10° C. The molten wax is poured into a container 25 mm in diameter and 20 mm deep. The wax is recrystallized at room temperature (25° C.) for 24 hours such that the surface of the wax is flat and smooth, and the wax is then stored for at least 1 hour at 20° C. before measuring the tack.

The texturometer spindle is displaced at a speed of 0.5 mm/s then penetrates the wax to a penetration depth of 2 mm. When the spindle has penetrated the wax to a depth of 2 mm, the spindle is held still for 1 second (corresponding to the relaxation time) and is then withdrawn at a speed of 0.5 mm/s.

During the relaxation time, the force (compression force) decreases greatly until it becomes zero, and then, during the withdrawal of the spindle, the force (stretching force) becomes negative and then rises again to the value 0. The tack corresponds to the integral of the curve of the force as a function of time for the part of the curve corresponding to the negative values of the force (stretching force). The tack value is expressed in N. s.

The tacky wax that may be used generally has a hardness of less than or equal to 3.5 MPa, in particular ranging from 0.01 MPa to 3.5 MPa, especially ranging from 0.05 MPa to 3 MPa or even ranging from 0.1 MPa to 2.5 MPa.

The hardness is measured according to the protocol described previously.

Tacky waxes that may be used include a $C_{20}$-$C_{40}$ alkyl (hydroxystearyloxy)stearate (the alkyl group containing from 20 to 40 carbon atoms), alone or as a mixture, in particular a $C_{20}$-$C_{40}$ alkyl 12-(12'-hydroxystearyloxy)stearate, of formula (II):

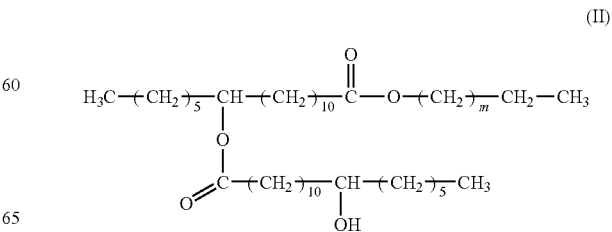

in which m is an integer ranging from 18 to 38, or a mixture of compounds of formula (II).

Such a wax is especially sold under the names "Kester Wax K 82 P®" and "Kester Wax K 80 P®" by the company Koster Keunen.

The waxes mentioned above generally have a starting melting point of less than 45° C.

The wax(es) may be in the form of an aqueous microdispersion of wax. The expression "aqueous microdispersion of wax" means an aqueous dispersion of wax particles in which the size of the said wax particles is less than or equal to about 1 μm.

Wax microdispersions are stable dispersions of colloidal wax particles, and are described especially in "Microemulsions Theory and Practice", L. M. Prince Ed., Academic Press (1977) pages 21-32.

In particular, these wax microdispersions may be obtained by melting the wax in the presence of a surfactant, and optionally of a portion of water, followed by gradual addition of hot water with stirring. The intermediate formation of an emulsion of the water-in-oil type is observed, followed by a phase inversion, with final production of a microemulsion of the oil-in-water type. On cooling, a stable microdispersion of solid wax colloidal particles is obtained.

The wax microdispersions may also be obtained by stirring the mixture of wax, surfactant and water using stirring means such as ultrasound, high-pressure homogenizers or turbomixers.

The particles of the wax microdispersion preferably have mean sizes of less than 1 μm (especially ranging from 0.02 μm to 0.99 μm) and preferably less than 0.5 μm (especially ranging from 0.06 μm to 0.5 μm).

These particles consist essentially of a wax or a mixture of waxes. However, they may comprise a small proportion of oily and/or pasty fatty additives, a surfactant and/or a common liposoluble additive/active agent.

The term "pasty fatty substance" means a lipophilic fatty compound comprising at a temperature of 23° C. a liquid fraction and a solid fraction.

The said pasty compound preferably has a hardness at 20° C. ranging from 0.001 to 0.5 MPa and preferably from 0.002 to 0.4 MPa.

The hardness is measured according to a method of penetration of a probe in a sample of compound and in particular using a texture analyzer (for example the TA-XT2i machine from Rheo) equipped with a stainless-steel spindle 2 mm in diameter. The hardness measurement is performed at 20° C. at the centre of-five samples. The spindle is introduced into each sample at a pre-speed of 1 mm/s and then at a measuring speed of 0.1 mm/s, the penetration depth being 0.3 mm. The hardness value revealed is that of the maximum peak.

The liquid fraction of the pasty compound measured at 23° C. preferably represents 9% to 97% by weight of the compound. This liquid fraction at 23° C. preferably represents between 15% and 85% and more preferably between 40% and 85% by weight. The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound to change from the solid state to the liquid state. The pasty compound is said to be in the solid state when all of its mass is in solid crystalline form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instrument, with a temperature rise of 5 or 10° C. per minute, according to standard ISO 11357-3:1999. The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 23° C., consisting of a liquid fraction and a solid fraction.

The liquid fraction of the pasty compound, measured at 32° C., preferably represents from 30% to 100% by weight of the compound, preferably from 80% to 100% and more preferably from 90% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same manner as the heat of fusion consumed at 23° C.

The gums are generally polydimethylsiloxanes (PDMS) of high molecular weight, cellulose gums or polysaccharide gums, and the pasty substances are generally hydrocarbon-based compounds, for instance lanolins and derivatives thereof, or PDMSs.

The nature and amount of the solid substances depend on the desired mechanical properties and textures. As a guide, the composition may contain from 0.1% to 50% by weight, better still from 1% to 40% and even better still from 5% to 30% by weight of waxes, relative to the total weight of the composition.

Besides the polymer dispersed in the liquid fatty phase described above according to the invention, the composition may comprise an additional polymer such as a film-forming polymer. According to the present invention, the term "film-forming polymer" means a polymer capable of forming, by itself or in the presence of an auxiliary film-forming agent, a continuous film that adheres to a support, especially to keratin materials.

Among the film-forming polymers that may be used in the composition of the present invention, mention may be made of synthetic polymers, of free-radical type or of polycondensate type, polymers of natural origin, and mixtures thereof. Film-forming polymers that may be mentioned in particular include acrylic polymers, polyurethanes, polyesters, polyamides, polyureas and cellulose-based polymers, for instance nitrocellulose.

The composition according to the invention may also comprise one or more dyestuffs chosen from water-soluble dyes, and pulverulent dyestuffs, for instance pigments, nacres and flakes that are well known to those skilled in the art. The dyestuffs may be present in the composition in a content ranging from 0.01% to 50% by weight and preferably from 0.01% to 30% by weight relative to the weight of the composition.

The term "pigments" should be understood as meaning white or coloured, mineral or organic particles of any form, which are insoluble in physiological medium, and which are intended to colour the composition.

The term "nacres" should be understood as meaning iridescent particles of any form, especially produced by certain molluscs in their shell, or alternatively synthesized.

The pigments may be white or coloured, and mineral and/or organic. Among the mineral pigments that may be mentioned are titanium dioxide, optionally surface-treated, zirconium oxide or cerium oxide, and also zinc oxide, iron oxide (black, yellow or red) or chromium oxide, manganese violet, ultramarine blue, chromium hydrate and ferric blue, and metal powders, for instance aluminium powder or copper powder. Among the organic pigments that may be mentioned are carbon black, pigments of D & C type, and lakes based on cochineal carmine or on barium, strontium, calcium or aluminium.

Mention may also be made of pigments with an effect, such as particles comprising a natural or synthetic, organic or mineral substrate, for instance glass, acrylic resins, polyester, polyurethane, polyethylene terephthalate, ceramics or aluminas, the said substrate possibly being coated with metallic substances, for instance aluminium, gold, silver, platinum, copper, bronze or metal oxides, for instance titanium dioxide, iron oxide or chromium oxide, and mixtures thereof.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment of the abovementioned type and also nacreous pigments based on bismuth oxychloride. It is also possible to use interference pigments, especially containing liquid crystals or multilayers.

In particular, it has been found that the use of the dispersion of particles of a non-silicone-based grafted ethylenic polymer in a liquid fatty phase, as described above, in a cosmetic composition comprising pulverulent dyestuffs, in particular pigments, allows good dispersion of the said pigments (without sedimentation) and thus good stability and good homogeneity of the colour of the composition according to the invention over time.

Accordingly, one subject of the present invention is a cosmetic composition comprising, in a cosmetically acceptable medium, a dispersion of particles of a non-silicone-based grafted ethylenic polymer in a liquid fatty phase and a pulverulent dyestuff, especially in the form of pigments.

The liposoluble dyestuffs are, for example, Sudan Red, D & C Red 17, D & C Green 6, β-carotene, soybean oil, Sudan Brown, D & C Yellow 11, D & C Violet 2, D & C Orange 5, quinoline yellow or annatto. The water-soluble dyes are, for example, beetroot juice, methylene blue, the disodium salt of ponceau, the disodium salt of alizarin green, quinoline yellow, the trisodium salt of amaranth, the disodium salt of tartrazine, the monosodium salt of rhodamine, the disodium salt of fuchsin, or xanthophyll.

The composition according to the invention may comprise at least one filler, especially in a content ranging from 0.01% to 50% by weight and preferably ranging from 0.01% to 30% by weight relative to the total weight of the composition. The term "fillers" should be understood as meaning colourless or white, mineral or synthetic particles of any form, which are insoluble in the medium of the composition irrespective of the temperature at which the composition is manufactured. These fillers serve especially to modify the rheology or texture of the composition.

The fillers may be mineral or organic and of any form, platelet-shaped, spherical or oblong, irrespective of the crystallographic form (for example lamellar, cubic, hexagonal, orthorhombic, etc). Mention may be made of talc, mica, silica, kaolin, polyamide powder, for instance Nylon® (Orgasol® from Atochem) poly-β-alanine powder and polyethylene powder, tetrafluoroethylene polymer powders, for instance Teflon®, lauroyllysine, starch, boron nitride, expanded hollow polymer microspheres such as those made of polyvinylidene chloride/acrylonitrile, for instance Expancel® (Nobel Industrie), acrylic acid copolymers (Polytrap® from Dow Corning) and silicone resin microbeads (for example Tospearls® from Toshiba), elastomeric polyorganosiloxane particles, precipitated calcium carbonate, magnesium carbonate, magnesium hydrocarbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc, magnesium or lithium stearate, zinc laurate or magnesium myristate.

The composition according to the invention may also contain ingredients commonly used in cosmetics, such as vitamins, thickeners, gelling agents, trace elements, softeners, sequestering agents, fragrances, acidifying or basifying agents, preserving agents, sunscreens, surfactants, antioxidants, fibres, agents for preventing hair loss, eyelash care agents, antidandruff agents and propellants, or mixtures thereof.

The term "fibre" should be understood as meaning an object of length L and diameter D such that L is very much greater than D, D being the diameter of the circle within which the cross section of the fibre is inscribed. In particular, the ratio L/D (or form factor) is chosen within the range from 3.5 to 2500, preferably from 5 to 500 and better still from 5 to 150.

In particular, the fibres have a length ranging from 1 μm to 10 mm, preferably from 0.1 mm to 5 mm and better still from 0.3 mm to 3 mm.

The fibres that may be used in the composition of the invention may be chosen from rigid and non-rigid fibres, and they may be of synthetic or natural, mineral or organic origin.

As fibres that may be used in the composition according to the invention, mention may be made of non-rigid fibres such as polyamide (Nylon®) fibres, or rigid fibres, such as polyimide-amide fibres, for instance those sold under the name "Kermel" or "Kermel Tech" by the company Rhodia, or poly (p-phenyleneterephthalamide) (or aramid) fibres, sold especially under the name Kevlar® by the company DuPont de Nemours.

The fibres may be present in the composition according to the invention in a content ranging from 0.1% to 10% by weight and better still from 0.5% to 5% by weight relative to the total weight of the composition.

The gelling agents that may be used in the compositions according to the invention may be organic or mineral, and polymeric or molecular, hydrophilic or lipophilic gelling agents.

Mineral lipophilic gelling agents that may be mentioned include optionally modified clays, for instance hectorites modified with a $C_{10}$ to $C_{22}$ fatty acid ammonium chloride, for instance hectorite modified with distearyldimethylammonium chloride, for instance the product sold under the name "Bentone 38V®" by the company Elementis.

Mention may also be made of fumed silica optionally subjected to a hydrophobic surface treatment, the particle size of which is less than 1 μm. Specifically, it is possible to chemically modify the surface of the silica, by chemical reaction generating a reduction in the number of silanol groups present at the surface of the silica. It is especially possible to substitute silanol groups with hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as "silica silylate" according to the CTFA (6th edition, 1995). They are sold, for example, under the references "Aerosil R812®" by the company Degussa, and "Cab-O-Sil TS-530®" by the company Cabot;

dimethylsilyloxyl or polydimethylsiloxane groups, which are obtained especially by treating fumed silica in the presence of polydimethylsiloxane or dimethyldichlorosilane. Silicas thus treated are known as "silica dimethyl silylate" according to the CTFA (6th edition, 1995). They are sold, for example, under the references "Aerosil R972®" and "Aerosil R974®" by the company Degussa, and "Cab-O-Sil TS-610®" and "Cab-O-Sil TS-720®" by the company Cabot.

The hydrophobic fumed silica particularly has a particle size that may be nanometric to micrometric, for example ranging from about 5 to 200 nm.

The polymeric organic lipophilic gelling agents are, for example, partially or totally crosslinked elastomeric organopolysiloxanes of three-dimensional structure, for instance those sold under the names "KSG6®", "KSG16®" and "KSG18®" from Shin-Etsu, "Trefil E-505C®" and "Trefil E-506C®" from Dow Corning, "Gransil SR-CYC®", "SR DMF 10®", "SR-DC556®", "SR 5CYC gel®", "SR DMF 10 gel®" and "SR DC 556 gel®" from Grant Industries and "SF 1204®" and "JK 113®" from General Electric; ethylcellulose, for instance the product sold under the name "Ethocel®" by Dow Chemical and galactomannans comprising from one to six and in particular from two to four hydroxyl groups per saccharide, substituted with a saturated or unsaturated alkyl chain, for instance guar gum alkylated with $C_1$ to $C_6$, and in particular $C_1$ to $C_3$, alkyl chains, and mixtures thereof. Block copolymers of "diblock" or "triblock" type, of the polystyrene/polyisoprene or polystyrene/polybutadiene type such as the products sold under the name "Luvitol HSB®" by the company BASF, of the polystyrene/copoly(ethylene-propylene) type such as the products sold under the name "Kraton®" by the company Shell Chemical Co., or of the polystyrene/copoly(ethylene-butylene) type.

Among the lipophilic gelling agents that may be used in the compositions according to the invention, mention may also be made of fatty acid esters of dextrin, such as dextrin palmitates, especially the products sold under the names "Rheopearl TL®" or "Rheopearl KL®" by the company Chiba Flour.

The lipophilic gelling agents may be present in the composition according to the invention in a content ranging from 0.05% to 40% by weight, preferably from 0.5% to 20% and better still from 1% to 15% by weight relative to the total weight of the composition.

Hydrophilic or water-soluble gelling agents that may be mentioned include:

homopolymers or copolymers of acrylic or methacrylic acid or the salts and esters thereof, and in particular the products sold under the names "Versicol F" or "Versicol K" by the company Allied Colloid, "Ultrahold 8" by the company Ciba-Geigy, and the polyacrylic acids of Synthalen K type;

copolymers of acrylic acid and of acrylamide sold in the form of the sodium salt thereof under the names "Reten" by the company Hercules, sodium polymethacrylate sold under the name "Darvan No. 7" by the company Vanderbilt, and the sodium salts of polyhydroxycarboxylic acids sold under the name "Hydagen F" by the company Henkel;

polyacrylic acid/alkyl acrylate copolymers of the Pemulen type;

AMPS (polyacrylamidomethylpropanesulfonic acid partially neutralized with ammonia and highly crosslinked) sold by the company Clariant;

AMPS/acrylamide copolymers of the Sepigel or Simulgel type, sold by the company SEPPIC, and AMPS/polyoxyethylenated alkyl methacrylate copolymers (crosslinked or non-crosslinked), and mixtures thereof.

As other examples of water-soluble gelling polymers, mention may be made of:

proteins, for instance proteins of plant origin, such as wheat or soybean proteins; proteins of animal origin such as keratins, for example keratin hydrolysates and sulfonic keratins;

anionic, cationic, amphoteric or nonionic chitin or chitosan polymers;

cellulose polymers such as hydroxyethylcellulose, hydroxypropylcellulose, methylcellulose, ethylhydroxyethylcellulose and carboxymethylcellulose, and also quaternized cellulose derivatives;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

associative polyurethanes such as the $C_{16}$-$OE_{120}$-$C_{16}$ polymer from the company Servo Delden (sold under the name Ser Ad FX1100, which is a molecule containing urethane functions and having a weight-average molecular weight of 1300), OE being an oxyethylene unit, Rheolate 205 containing urea functions, sold by the company Rheox, or Rheolate 208 or 204 (these polymers being sold in pure form) or DW 1206B from Röhm & Haas, containing a $C_{20}$ alkyl chain and a urethane bond, sold at a solids content of 20% in water. It is also possible to use solutions or dispersions of these associative polyurethanes, especially in water or in aqueous-alcoholic medium. Examples of such polymers that may be mentioned include Ser Ad FX1010, Ser Ad FX1035 and Ser Ad 1070 from the company Servo Delden, and Rheolate 255, Rheolate 278 and Rheolate 244 sold by the company Rheox. It is also possible to use the product DW 1206F and DW 1206J, and also Acrysol RM 184 or Acrysol 44 from the company Röhm & Haas, or Borchigel LW 44 from the company Borchers;

optionally modified polymers of natural origin, such as:
gum arabics, guar gum, xanthan derivatives and karaya gum,
alginates and carrageenans;
glycoaminoglycans, and hyaluronic acid and its derivatives;
shellac resin, sandarac gum, dammar resins, elemi gums and copal resins;
deoxyribonucleic acid;
mucopolysaccharides such as hyaluronic acid and chondroitin sulfates, and mixtures thereof.

The hydrophilic gelling agents may be present in the composition according to the invention in a content ranging from 0.05% to 20% by weight, preferably from 0.5% to 10% and better still from 0.8% to 5% by weight relative to the total weight of the composition.

The composition according to the invention may contain emulsifying surfactants, which are especially present in a proportion ranging from 0.5% to 30% by weight, better still from 2% to 15% and even better still from 3% to 10% relative to the total weight of the composition. These surfactants may be chosen from anionic, cationic and nonionic surfactants. Reference may be made to the document "Encyclopedia of Chemical Technology, Kirk-Othmer", Volume 22, pp. 333-

432, 3rd Edition, 1979, Wiley, for the definition of the properties and functions (emulsifying) of surfactants, in particular pp. 347-377 of this reference, for the anionic and nonionic surfactants.

The surfactants preferably used in the composition according to the invention are chosen from:

a) nonionic surfactants with an HLB of greater than or equal to 8 at 25° C., used alone or as a mixture; mention may be made especially of:

oxyethylenated and/or oxypropylenated ethers (which may comprise from 1 to 150 oxyethylene and/or oxypropylene groups) of glycerol;

oxyethylenated and/or oxypropylenated ethers (which may comprise from 1 to 150 oxyethylene and/or oxypropylene groups) of fatty alcohols (especially of $C_8$-$C_{24}$ and preferably $C_{12}$-$C_{18}$ alcohol), such as oxyethylenated cetearyl alcohol ether containing 30 oxyethylene groups (CTFA name "Ceteareth-30") and the oxyethylenated ether of the mixture of $C_{12}$-$C_{15}$ fatty alcohols comprising 7 oxyethylene groups (CTFA name "C12-15 Pareth-7" sold under the name "Neodol 25-7"® by Shell Chemicals);

fatty acid esters (especially of a $C_8$-$C_{24}$ and preferably $C_{16}$-$C_{22}$ acid) of polyethylene glycol (which may comprise from 1 to 150 ethylene glycol units), such as PEG-50 stearate and PEG-40 monostearate sold under the name Myrj 52P by the company ICI Uniqema;

fatty acid esters (especially of a $C_8$-$C_{24}$ and preferably $C_{16}$-$C_{22}$ acid) of oxyethylenated and/or oxypropylenated glyceryl ethers (which may comprise from 1 to 150 oxyethylene and/or oxypropylene groups), for instance PEG-200 glyceryl monostearate sold under the name "Simulsol 220 TM" by the company SEPPIC; glyceryl stearate polyethoxylated with 30 ethylene oxide groups, for instance the product Tagat S sold by the company Goldschmidt, glyceryl oleate polyethoxylated with 30 ethylene oxide groups, for instance the product Tagat O sold by the company Goldschmidt, glyceryl cocoate polyethoxylated with 30 ethylene oxide groups, for instance the product Varionic LI 13 sold by the company Sherex, glyceryl isostearate polyethoxylated with 30 ethylene oxide groups, for instance the product Tagat L sold by the company Goldschmidt, and glyceryl laurate polyethoxylated with 30 ethylene oxide groups, for instance the product Tagat I from the company Goldschmidt;

fatty acid esters (especially of a $C_8$-$C_{24}$ and preferably $C_{16}$-$C_{22}$ acid) of oxyethylenated and/or oxypropylenated sorbitol ethers (which may comprise from 1 to 150 oxyethylene and/or oxypropylene groups), for instance polysorbate 60 sold under the name "Tween 60" by the company Uniqema;

dimethicone copolyol, such as the product sold under the name "Q2-5220" by the company Dow Corning, dimethicone copolyol benzoate (Finsolv SLB 101 and 201 by the company Finetex), copolymers of propylene oxide and of ethylene oxide, also known as EO/PO polycondensates, for instance the polyethylene glycol/polypropylene glycol/polyethylene glycol triblock polycondensates sold under the names "Synperonic", for instance "Synperonic PE/L44" and "Synperonic PE/F127", by the company ICI, and mixtures thereof, and mixtures thereof.

b) nonionic surfactants with an HLB of less than 8 at 25° C., optionally combined with one or more nonionic surfactants with an HLB of greater than 8 at 25° C., as mentioned above, such as:

saccharide esters and ethers, such as sucrose stearate, sucrose cocoate and sorbitan stearate, and mixtures thereof, for instance Arlatone 2121 sold by the company ICI;

fatty acid esters (especially of a $C_8$-$C_{24}$ and preferably $C_{16}$-$C_{22}$ acid) of polyols, especially of glycerol or of sorbitol, such as glyceryl stearate, glyceryl stearate such as the product sold under the name Tegin M by the company Goldschmidt, glyceryl laurate such as the product sold under the name Imwitor 312 by the company Hüls, polyglyceryl-2 stearate, sorbitan tristearate or glyceryl ricinoleate;

the mixture of cyclomethicone/dimethicone copolyol sold under the name "Q2-3225C" by the company Dow Corning.

c) anionic surfactants such as:

$C_{16}$-$C_{30}$ fatty acid salts, especially those derived from amines, for instance triethanolamine stearate;

polyoxyethylenated fatty acid salts, especially those derived from amines or alkali metal salts, and mixtures thereof;

phosphoric esters and salts thereof, such as "DEA oleth-10 phosphate" (Crodafos N 10N from the company Croda);

sulfosuccinates such as "Disodium PEG-5 citrate lauryl sulfosuccinate" and "Disodium ricinoleamido MEA sulfosuccinate";

alkyl ether sulfates, such as sodium lauryl ether sulfate;

isethionates;

acylglutamates such as "Disodium hydrogenated tallow glutamate" (Amisoft HS-21 R sold by the company Ajinomoto), and mixtures thereof.

Triethanolamine stearate is most particularly suitable for the invention. This is generally obtained by simple mixing of stearic acid and triethanolamine.

Surfactants that allow an oil-in-water or wax-in-water emulsion to be obtained are preferably used.

Needless to say, a person skilled in the art will take care to select this or these optional additional compound(s), and/or the amount thereof, such that the advantageous properties of the corresponding composition according to the invention are not, or are not substantially, adversely affected by the envisaged addition.

The composition according to the invention may comprise an aqueous medium, constituting an aqueous phase, which may form the continuous phase of the composition.

The aqueous phase may consist essentially of water; it may also comprise a mixture of water and of water-miscible solvent (miscibility in water of greater than 50% by weight at 25° C.), for instance lower monoalcohols containing from 1 to 5 carbon atoms such as ethanol or isopropanol, glycols containing from 2 to 8 carbon atoms such as propylene glycol, ethylene glycol, 1,3-butylene glycol and dipropylene glycol, $C_3$-$C_4$ ketones and $C_2$-$C_4$ aldehydes, and mixtures thereof.

The aqueous phase (water and optionally the water-miscible solvent) may be present in a content ranging from 0.1% to 95% by weight and preferably ranging from 1% to 80% by weight relative to the total weight of the composition.

The composition according to the invention may especially be in the form of a suspension, a dispersion, a solution, a gel, an emulsion, especially an oil-in-water (O/W) or water-in-oil (W/O) emulsion, or a multiple emulsion (W/O/W, polyol/O/W or O/W/O), in the form of a cream, a paste, a mousse, a vesicular dispersion, especially of ionic or nonionic lipids, a two-phase or multi-phase lotion, a spray, a powder, a paste, especially a soft paste (especially a paste with a dynamic viscosity at 25° C. of about from 0.1 to 40 Pa·s under a shear rate of 200 s$^{-1}$, after 10 minutes of measurement in cone/plate geometry). The composition may be anhydrous; for example, it may be an anhydrous paste or stick. The composition may be a leave-in composition.

A person skilled in the art may select the appropriate galenical form, and also the method for preparing it, on the basis of his general knowledge, taking into account firstly the nature of the constituents used, especially their solubility in the support, and secondly the intended use of the composition.

According to another aspect, the invention also relates to a cosmetic assembly comprising:

i) a container delimiting at least one compartment, the said container being closed by a closing member; and ii) a composition placed inside the said compartment, the composition being in accordance with any one of the claims hereinbelow.

The container may be in any adequate form. It may especially be in the form of a bottle, a tube, a jar, a case, a box, a sachet or a carton.

The closing member may be in the form of a removable stopper, a lid, a cap, a tear-off strip or a capsule, especially of the type comprising a body attached to the container and a cover cap articulated on the body. It may also be in the form of a member for selectively closing the container, especially a pump, a valve or a flap valve.

The container may be combined with an applicator, especially in the form of a brush comprising an arrangement of bristles maintained by a twisted wire. Such a twisted brush is described especially in patent U.S. Pat. No. 4,887,622. It may also be in the form of a comb comprising a plurality of application members, obtained especially by moulding. Such combs are described, for example, in patent FR 2 796 529. The applicator may be in the form of a fine brush, as described, for example, in patent FR 2 722 380. The applicator may be in the form of a block of foam or of elastomer, a felt or a spatula. The applicator may be free (tuft or sponge) or securely fastened to a rod borne by the closing member, as described, for example, in patent U.S. Pat. No. 5,492,426. The applicator may be securely fastened to the container, as described, for example, in patent FR 2 761 959.

The product may be contained directly in the container, or indirectly. By way of example, the product may be arranged on an impregnated support, especially in the form of a wipe or a pad, and arranged (individually or in plurality) in a box or in a sachet. Such a support incorporating the product is described, for example, in patent application WO 01/03538.

The closing member may be coupled to the container by screwing. Alternatively, the coupling between the closing member and the container is done other than by screwing, especially via a bayonet mechanism, by click-fastening, gripping, welding, bonding or by magnetic attraction. The term "click-fastening" in particular means any system involving the crossing of a bead or cord of material by elastic deformation of a portion, especially of the closing member, followed by return to the elastically unconstrained position of the said portion after the crossing of the bead or cord.

The container may be at least partially made of thermoplastic material. Examples of thermoplastic materials that may be mentioned include polypropylene or polyethylene.

Alternatively, the container is made of non-thermoplastic material, especially glass or metal (or alloy).

The container may have rigid walls or deformable walls, especially in the form of a tube or a tubular bottle.

The container may comprise means for distributing or facilitating the distribution of the composition. By way of example, the container may have deformable walls so as to cause the composition to exit in response to a positive pressure inside the container, this positive pressure being caused by elastic (or non-elastic) squeezing of the walls of the container. Alternatively, especially when the product is in the form of a stick, the product may be driven out by a piston mechanism. Still in the case of a stick, especially of makeup product (lipstick, foundation, etc.), the container may comprise a mechanism, especially a rack mechanism, a threaded-rod mechanism or a helical groove mechanism, and may be capable of moving a stick in the direction of the said aperture. Such a mechanism is described, for example, in patent FR 2 806 273 or in patent FR 2 775 566. Such a mechanism for a liquid product is described in patent FR 2 727 609.

The container may consist of a carton with a base delimiting at least one housing containing the composition, and a lid, especially articulated on the base, and capable of at least partially covering the said base. Such a carton is described, for example, in patent application WO 03/018423 or in patent FR 2 791 042.

The container may be equipped with a drainer arranged in the region of the aperture of the container. Such a drainer makes it possible to wipe the applicator and possibly the rod to which it may be securely fastened. Such a drainer is described, for example, in patent FR 2 792 618.

The composition may be at atmospheric pressure inside the container (at room temperature) or pressurized, especially by means of a propellent gas (aerosol). In the latter case, the container is equipped with a valve (of the type used for aerosols).

The content of the patents or patent applications mentioned above is incorporated by reference into the present patent application.

The invention is illustrated in greater detail by the examples described below.

EXAMPLES 1 AND 2

Preparation of a Dispersion of Polymer Particles

Examples 1 and 2 illustrate the preparation of polymers in accordance with the invention, capable of forming a dispersion of particles in an organic medium under consideration.

In these examples, after preparing the said dispersion, the weight-average (Mw) and number-average (Mn) molar masses of the polymer, the glass transition temperature of the polymer, the solids content (or dry extract) of the dispersion and the size of the polymer particles are determined.

The weight-average (Mw) and number-average (Mn) molar masses are determined by gel-permeation liquid chromatography (THF solvent, calibration curve established with linear polystyrene standards, refractometric detector).

The measurement of the glass transition temperature (Tg) is performed according to standard ASTM D3418-97, by differential thermal analysis (DSC "Differential Scanning Calorimetry") on a calorimeter, over a temperature range of between −100° C. and +150° C., at a heating rate of 10° C./minute in 150 µl aluminium crucibles.

The crucibles are prepared in the following manner: 100 µl of the dispersion obtained are introduced into a 150 µl aluminium crucible and the solvent is allowed to evaporate over 24 hours at room temperature and at 50% RH. The operation is repeated and the crucible is then introduced into a Mettler DSC30 calorimeter.

The solids content (or dry extract), i.e. the amount of non-volatile matter, may be measured in various ways: mention may be made, for example, of the methods by oven-drying or the methods by drying by exposure to infrared radiation.

The solids content of the polymer dispersion obtained is preferably measured by heating the sample with infrared rays with a wavelength of from 2 μm to 3.5 μm. The substances contained in the composition that have a high vapour pressure evaporate under the effect of this radiation. Measuring the weight loss of the sample makes it possible to determine the dry extract of the composition. These measurements are performed using an LP16 commercial infrared desiccator from Mettler. This technique is fully described in the documentation for the machine supplied by Mettler.

The measuring protocol is as follows: about 1 g of the dispersion is spread onto a metal cup. After introducing this cup into the desiccator, it is subjected to a nominal temperature of 120° C. for 1 hour. The wet mass of the sample, corresponding to the initial mass, and the dry mass of the sample, corresponding to the mass after exposure to the radiation, are measured using a precision balance.

The solids content is calculated in the following manner:

dry extract=100×(dry mass/wet mass).

The particle sizes may be measured by various techniques; mention may be made in particular of light-scattering techniques (dynamic and static), Coulter counter methods, sedimentation rate measurements (related to the size via Stokes' law) and microscopy. These techniques make it possible to measure a particle diameter and, for some of them, a particle size distribution.

The sizes and size distributions of the particles in the compositions according to the invention are preferably measured by static light scattering using a commercial granulometer such as the MasterSizer 2000 from Malvern. The data are processed on the basis of the Mie scattering theory. This theory, which is exact for isotropic particles, makes it possible to determine an "effective" particle diameter in the case of non-spherical particles. This theory is described especially in the publication by Van de Hulst, H. C., "Light Scattering by Small Particles," Chapters 9 and 10, Wiley, New York, 1957.

The composition is characterized by its mean "effective" diameter by volume D[4.3], defined in the following manner:

$$D[4.3] = \frac{\sum_i V_i \cdot d_i}{\sum_i V_i}$$

in which $V_i$ represents the volume of the particles with an effective diameter $d_i$. This parameter is described especially in the technical documentation of the granulometer.

The measurements are performed at 25° C. on a dilute particle dispersion, obtained from the composition in the following manner: 1) dilution by a factor of 100 with water, 2) homogenization of the solution, 3) standing of the solution for 18 hours, 4) recovery of the whitish uniform supernatant.

The "effective" diameter is obtained by taking a refractive index of 1.33 for water and a mean refractive index of 1.42 for the particles.

EXAMPLE 1

This example illustrates the preparation of a dispersion of particles of a polymer in isododecane, the said polymer being obtained by polymerization of methyl acrylate and the corresponding macromonomer with a polyethylene/polybutylene copolymer containing methacrylate end groups (Kraton L-1253).

2 kg of heptane, 2 kg of isododecane, 2.8 kg of methyl acrylate and 1.2 kg of macromonomer of the polyethylene/polybutylene copolymer type containing methacrylate end groups (Kraton L-1253) and 320 g of tert-butyl peroxy-2-ethylhexanoate (Trigonox 21S) are loaded into a reactor.

The reaction mixture is stirred and heated from room temperature to 90° C. over 1 hour. After 15 minutes at 90° C., a change is observed in the appearance of the reaction medium, which passes from a transparent appearance to a milky appearance. Heating with stirring is continued for a further 15 minutes, and a mixture consisting of 16 kg of methyl acrylate and 200 g of Trigonox 21S is then added dropwise over 1 hour.

Next, the mixture is heated for 4 hours at 90° C. and the heptane is then distilled from the reaction medium. After this distillation operation, a stable dispersion of particles of polymer thus prepared in isododecane is obtained.

The grafted polymer comprises 6% by weight of macromonomer relative to the weight of the polymer.

The characteristics of the polymer and of the particles formed by the said polymer are as follows:
weight-average molecular mass Mw=119 900
number-average molecular mass Mn=16 300
polydispersity index (Mw/Mn)=7.37
glass transition: 10° C. by Mettler DSC;
dry extract: 52.4% in isododecane, performed by thermobalance;
particle size: 46 nm with polydispersity of 0.05, performed on a Malvern Autosizer Lo-C at 25° C.

The stability of the dispersion obtained is demonstrated by performing the following stability protocol: 8 ml of the dispersion prepared are placed in a haemolysis tube and centrifuged at 4000 rpm for 15 minutes using a Jouan C100-S5 centrifuge. After 15 minutes, it is found that there is no phase separation, which demonstrates that the dispersion is stable.

EXAMPLE 2

This example illustrates the preparation of a polymer forming a dispersion of particles in a carbon-based solvent, the said polymer being obtained by polymerization of methyl acrylate, acrylic acid and the corresponding macromonomer with a polyethylene/polybutylene copolymer containing methacrylate end groups (Kraton L-1253).

200 g of heptane, 200 g of isododecane, 28 g of methyl acrylate and 12 g of macromonomer of the polyethylene/polybutylene copolymer type containing methacrylate end groups (Kraton L-1253) and 3.2 g of tert-butyl peroxy-2-ethylhexanoate (Trigonox 21S) are loaded into a 1 litre reactor.

The reaction mixture is stirred and heated from room temperature to 90° C. over 1 hour. After 15 minutes at 90° C., a change is observed in the appearance of the reaction medium, which passes from a transparent appearance to a milky appearance. Heating with stirring is continued for a further 15 minutes, and a mixture consisting of 150 g of methyl acrylate, 10 g of acrylic acid and 2 g of Trigonox 21S is then added dropwise over 1 hour.

Next, the mixture is heated for 4 hours at 90° C. and the heptane is then distilled from the reaction medium. After this distillation operation, a stable dispersion of particles of polymer thus prepared in isododecane is obtained.

The grafted polymer comprises 6% by weight of macromonomer relative to the weight of the polymer.

The characteristics of the polymer and of the particles formed by the said polymer are as follows:

weight-average molecular mass Mw=143 639 number-average molecular mass Mn=23 965 polydispersity index (Mw/Mn)=5.99 theoretical dry extract: 51.3% in isododecane particle size: 48 nm with polydispersity of 0.04, performed on a Malvern Autosizer Lo-C at 25° C.

After performing the stability protocol in accordance with Example 1, it is found that the dispersion obtained is stable.

EXAMPLE 3

Tube of Lipstick

| Ingredients INCI name | mass % |
| --- | --- |
| Octyldodecanol | 11.75 |
| VP eicosene copolymer | 15 |
| Polyethylene (polyethylene wax MW 500) | 13 |
| Pigments | 10.25 |
| Polymer dispersion of Example 1 | 50 |

The wax, the oily phase and the pigments in the form of ground material are introduced into the oily phase containing the PVP eicosene, in a heating pan. The mixture is melted at 100° C. with stirring using a Rayneri mixer. When the preparation is liquid, the mixture is left at 100° C. for 40 minutes. The volatile ingredients or ingredients containing volatile solvents are then introduced. The heating pan is covered to limit evaporation and the mixture is left stirring for 10 minutes. The formulation is then cast at 42° C., and then placed in a freezer. The product is removed from the mould when the temperature of the mould is about 4° C.

The transfer of this formula was measured according to the protocol described above. It is equal to 1.85±0.1.

EXAMPLE 4

Tube of Lipstick

| Ingredients | mass % |
| --- | --- |
| Pigments | 8.20 |
| Hydrogenated polyisobutene (Parleam) | 5.18 |
| Polyhydroxystearic acid | 0.21 |
| C30-C50 alcohols | 2 |
| Polyethylene (polyethylene wax MW 500) | 10 |
| Sucrose acetate isobutyrate | 5 |
| Polymer dispersion of Example 1 | 68.82 |
| Fragrance | qs 100 |

Procedure

The waxes, the pigmentary pastes and the sucrose ester are introduced into a heating pan, with stirring using a Rayneri mixer, the mixture is brought to 105° C. and stirred for 30 minutes, the nacres are then added, the polymer dispersion and the fragrance are then added, and the mixture is stirred for 10 minutes and then poured into a mould at 42° C. The mould is placed in a freezer and the product is removed from the mould when the mould is at about 4° C. The transfer measured according to the protocol described above is equal to 1.2.

EXAMPLE 5

Tube of Lipstick

| Ingredients INCI name | mass % |
| --- | --- |
| Octyldodecanol | 11.75 |
| VP eicosene copolymer | 15 |
| Polyethylene (polyethylene wax MW 500) | 13 |
| Pigments | 10.25 |
| Polymer dispersion of Example 2 | 50 |

This composition was prepared according to the same procedure as that of Example 1.

EXAMPLE 6

Mascara

| Phase A | |
| --- | --- |
| Candelilla wax | 15% |
| Stearic acid | 5.8% |
| Dispersion of polymer of Example 2 | 10% |
| Phase B | |
| Triethanolamine | 2.9% |
| Hydroxyethylcellulose | 0.9% |
| Gum Arabic | 3.5% |
| Black iron oxide | 8% |
| Preserving agents | qs % |
| Water | qs 100 |

Procedure

This composition may be prepared in a standard manner by hot formation of a wax-in-water emulsion.

The fatty phase (phase A) containing the wax and the stearic acid is heated until the mixture of constituents has completely melted. Next, the dispersion of polymer of Example 2 and the pigments are incorporated with stirring into the oily phase. In parallel, the aqueous phase (phase B) containing the neutralizer (triethanolamine) and the gelling polymers is brought to a temperature at least equal to the temperature of the fatty phase. The aqueous phase is then added to the oily phase, with vigorous stirring (3000 rpm) to form the hot emulsion. Stirring and the temperature are maintained for about 30 minutes.

Moderate paddle stirring is then applied until the mixture has cooled to room temperature.

The invention claimed is:

1. A cosmetic composition for making up lips or skin comprising, in a cosmetically acceptable medium, a dispersion of particles, in a liquid fatty phase, of at least one nonsilicone-based grafted ethylenic polymer wherein the non-silicone-based grafted polymer is chosen from polymers obtained by polymerization:
- of methyl acrylate and of at least one polyethylene/polybutylene macromonomer comprising at least one methacrylate end group;
- of methoxyethyl acrylate and of at least one polyethylene/polybutylene macromonomer comprising at least one methacrylate end group;
- of methyl acrylate/methyl methacrylate monomers and of at least one polyethylene/polybutylene macromonomer comprising at least one methacrylate end group;
- of methyl acrylate/acrylic acid monomers and of at least one polyethylene/polybutylene macromonomer comprising at least one methacrylate end group;
- of methyl acrylate/dimethylaminoethyl methacrylate monomers and of at least one polyethylene/polybutylene macromonomer comprising at least one methacrylate end group;
- of methyl acrylate/2-hydroxyethyl methacrylate monomers and of at least one polyethylene/polybutylene macromonomer comprising at least one methacrylate end group; wherein said at least one non-silicone-based grafted ethylenic polymer is present in an amount sufficient to render the composition capable of forming a deposit with a transfer index of less than or equal to 35%.

2. A composition according to claim 1, further comprising at least one volatile oil chosen from isododecane, isodecane, and isohexadecane.

3. A composition according to claim 1, further comprising at least one non-volatile oil.

4. A composition according to claim 1, wherein the at least one non-silicone-based grafted ethylenic polymer in a liquid fatty phase consists of at least 50% by weight of at least one non-silicone-based liquid organic compound chosen from:
- non-silicone-based liquid organic compounds with a global solubility parameter according to the Hansen solubility space of less than or equal to 18 $(MPa)^{1/2}$;
- liquid monoalcohols with a global solubility parameter according to the Hansen solubility space of less than or equal to 20 $(MPa)^{1/2}$; and
- mixtures thereof.

5. A composition according to claim 1, wherein the at least one non-silicone-based grafted ethylenic polymer has a solids content ranging from 1% to 70% by weight, relative to the total weight of the composition.

6. A composition according to claim 1, further comprising from 0.1% to 50% by weight of waxes relative to the total weight of the composition.

7. A composition according to claim 1, further comprising at least one dyestuff.

8. A non-therapeutic cosmetic process for making up lips or skin comprising the application to the lips or skin a composition according to claim 1.

* * * * *